United States Patent [19]
Herlevi et al.

[11] Patent Number: 6,109,460
[45] Date of Patent: Aug. 29, 2000

[54] SUSPENSION RACK

[75] Inventors: Matti Herlevi, Porvoo; Ari Nenye, Helsinki, both of Finland

[73] Assignee: Instrumentarium Corporation, Helsinki, Finland

[21] Appl. No.: 09/101,854

[22] PCT Filed: Nov. 26, 1997

[86] PCT No.: PCT/FI97/00731

§ 371 Date: Jul. 17, 1998

§ 102(e) Date: Jul. 17, 1998

[87] PCT Pub. No.: WO98/23523

PCT Pub. Date: Jun. 4, 1998

[30] Foreign Application Priority Data

Nov. 26, 1996 [FI] Finland ................................ 964713

[51] Int. Cl.[7] ....................................................... A47F 7/00
[52] U.S. Cl. .................. 211/85.13; 211/60.1; 211/89.01; 211/106; 248/68.1
[58] Field of Search ................................ 211/106, 181.1, 211/119, 85.13, 13.1, 113, 89.01, 120, 60.1, 87.01; 248/68.1

[56] References Cited

U.S. PATENT DOCUMENTS

| | | |
|---|---|---|
| D. 25,926 | 8/1896 | Elliston . |
| 2,099,507 | 11/1937 | Wright ...................................... 211/106 |
| 3,115,107 | 12/1963 | Glenny ................................. 211/106 X |
| 3,217,891 | 11/1965 | Weaver . |
| 3,722,843 | 3/1973 | Enckler . |
| 4,886,173 | 12/1989 | Goulter ................................. 211/89.01 |
| 5,020,759 | 6/1991 | Weber . |
| 5,209,441 | 5/1993 | Satoh .................................. 248/68.1 X |
| 5,224,674 | 7/1993 | Simons . |
| 5,727,697 | 3/1998 | Ricciardelli et al. ................. 211/89.01 |

FOREIGN PATENT DOCUMENTS

| | | |
|---|---|---|
| 626 534 | 11/1994 | European Pat. Off. . |
| 95/11399 | 8/1994 | WIPO . |

*Primary Examiner*—Robert W. Gibson, Jr.
*Attorney, Agent, or Firm*—Andrus, Sceales, Starke & Sawall

[57] ABSTRACT

A suspension rack in medical use, such as for the storage and suspension of cables (1) and/or tubes for equipment used in patient monitoring, anesthesia, and the like, said rack including a frame (2) provided with fastening means (3) for securing the frame to a substantially solid structure (4) and with frame-connected members for the suspension of cables and/or tubes. The frame (2) includes a bracket element (5). The members for the suspension of cables and/or tubes consist of a cluster of mutually parallel, side-by-side spacer elements (6), connected with the bracket element and spaced from each other by a distance which exceeds the thickness of a cable and/or tube yet is less than the dimension of a terminal element (7), such as a connector or a sensor unit, mounted on the end of a cable and/or a tube, transverse to the lengthwise direction of a cable and/or a tube, the cable and/or tube being mountable between two adjacent spacer elements with the terminal element finding its way to said two adjacent specer elements.

14 Claims, 4 Drawing Sheets

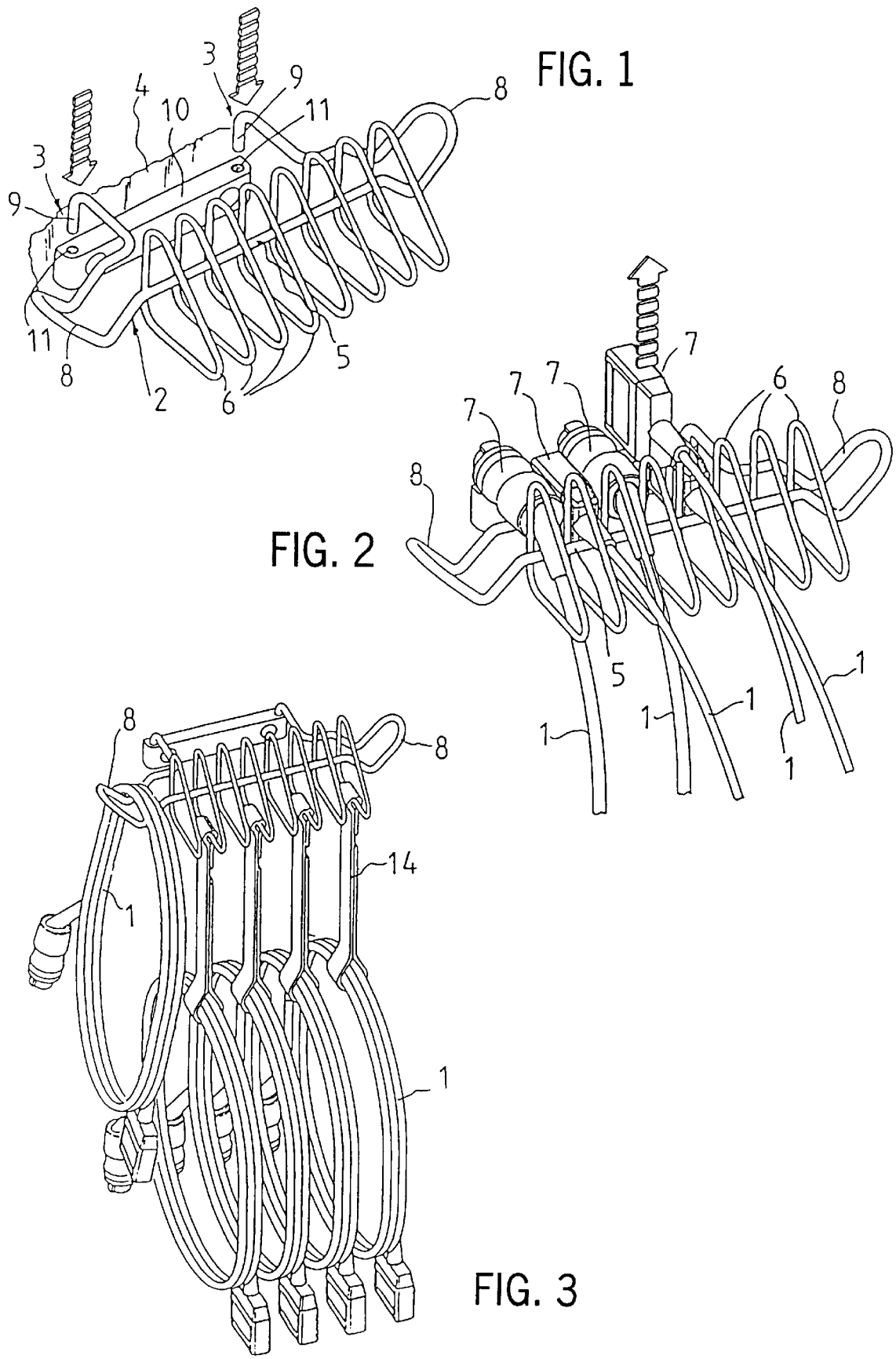

SUSPENSION RACK

The present invention relates to a suspension rack as defined the claims.

Prior known is a suspension rack in medical use. such as for the storage and suspension of cables and/or tubes for equipment used in patient monitoring, anesthesia, and the like. The rack includes a frame provided with fastening means for securing the frame to a substantially solid structure and with frame-connected members for the suspension of cables and/or tubes.

The handling of various cables and tubes is perceived by hospital staff as a major nuisance in terms of working with equipment and patients. The patient is often hooked up in a multitude of cables and tubes for monitoring and nursing the vital functions of a patient. The orderly management of cables and tubes is difficult in conditions, which constantly require the attachment, detachment, removal, and cleaning of cables and/or tubes.

When solving such problems, it is necessary to find ways and means for the orderly management of cables during the use and non-use thereof.

A particular problem lies in the necessity of setting up the cables and tubes readily in a proper order between the using periods and during the course of and after cleaning operations. In addition, they must be readily reusable without a hazard of entanglement or confusion.

A variety of attempts have been made to solve the above problems. Various arms have been used, mainly for guiding cables and tubes from the apparatus they are connected with to the application site thereof in such a way that they do not sag in disarray on the floor to be trampled on. Such arms are often provided with a number of hinges for adjusting the position thereof and with various holders or hooks for the suspension of cables and tubes.

At least one of the problems with these solutions, in terms of the orderly management, storage, use, and cleaning of cables, is the price thereof. In addition, it is possible that cables intertwine in such equipment. The disengagement of cables from the arms and the attachment thereof is tedious. Furthermore, such solutions require special attachment points or elements suspended from the apparatus.

There are also a variety of hook solutions for the storage of cables and tubes, ranging from individual hooks to arrays of hooks, placed e.g. on the wall or under the mattress. At least the following aspects can be considered as problems in such hook solutions. The hooks can be sharp and inflict injuries. A single hook can only be accommodated with a single cable in order to maintain a good order, as several cables or tubes on top of each other may cause disarray. As for the arrys of hooks, the spools of cable or tube do not keep in a manageable order and generally require a screw fastening for attaching the same to some solid structure.

Crates and boxes, often used for storing cables and tubes, are inconvenient in occupying shelf or other space, are difficult to keep clean, and cables and tubes become entangled with each other.

BRIEF SUMMARY OF THE INVENTION

An object of the invention is to eliminate the above drawbacks.

A particular object of the invention is to introduce a suspension rack, on which the cables can be readily suspended without a hazard of entanglement.

A further object of the invention is to introduce a suspension rack, which is attractive in terms of its price, versatile, safe, easy to use, durable, reasonably compact, easy to clean and, if necessary, fastenable to a variety of locations, such as horizontal and vertical surfaces and pipes.

A suspension rack of the invention is characterized by what is set forth in claim 1.

According to the invention, the frame includes a bracket element and the implements for suspending cables and/or tubes include a cluster of adjacent spacer elements, which are connected to the bracket element and spaced from each other by a distance that exceeds the thickness of a cable and/or a tube and is less than the dimension of a terminal element, such as a connector or a sensor unit, mounted on the end of a cable and/or a tube, transverse to the lengthwise direction of a cable and/or a tube, said cable and/or tube being insertable between two adjacent spacer elements with said terminal element finding its way to said two adjacent spacer elements.

An advantage gained by the invention is that individual cables and/or tubes can be suspended on the rack in an orderly fashion without a hazard of entanglement or confusion. In addition, the rack is attractive in terms of its price, versatile, safe, easy to use, durable, reasonably compact, and easy to clean.

In one embodiment of the rack, the bracket element is adapted to support a cable and/or a tube from below.

In one embodiment of the rack, the spacer elements are parallel to each other.

In one embodiment of the rack, the frame includes a hook, which is located beside the cluster of spacer elements and on which hook a cable, a spool of cable, a tube and/or a spool of tube is suspendable.

In one embodiment of the rack, the frame includes two hooks, which are mounted on either side of the cluster of spacer elements.

In one embodiment of the rack, the fastening means include two mutually parallel, spaced-apart fingers and a mounting fastenable to a solid structure and including fasteners which are adapted to receive the fingers therein. In one embodiment of the rack, the mounting is made from a thin sheet metal and the mounting sheet is provided with a bending line for bending the mounting to an angular form therealong.

In one embodiment of the rack, the solid structure, to which the mounting is fastened, comprises a pipe, a pole or the like; the mounting is a U-shaped element adapted to receive the pipe, the pole or the like therein; and the mounting is provided with a clamping screw for fastening the mounting to the pipe, the pole or the like thereby.

In one embodiment of the rack, the frame is constituted by a metal wire or a plastic wire.

In one embodiment of the rack, the spacer elements are constituted by a metal wire or a plastic wire.

In one embodiment of the rack, the spacer elements are in the form of a loop.

In one embodiment of the rack, the suspension rack includes a bracket, which is removably suspendable on a loop-shaped spacer element and on which bracket a spool of cable is removably mountable.

BRIEF DESCRIPTION OF THE SEVERAL VIEWS OF THE DRAWINGS

The invention will now be described in detail by means of application examples with reference made to the accompanying drawing, in which FIG. 1 shows a rack of the invention in a first embodiment, FIG. 2 shows the embodiment of FIG. 1 with cables suspended on the rack, FIG. 3 shows the embodiment of FIG. 1 with a spool of cable suspended on the rack.

DETAILED DESCRIPTION OF THE INVENTION

Figure 4:
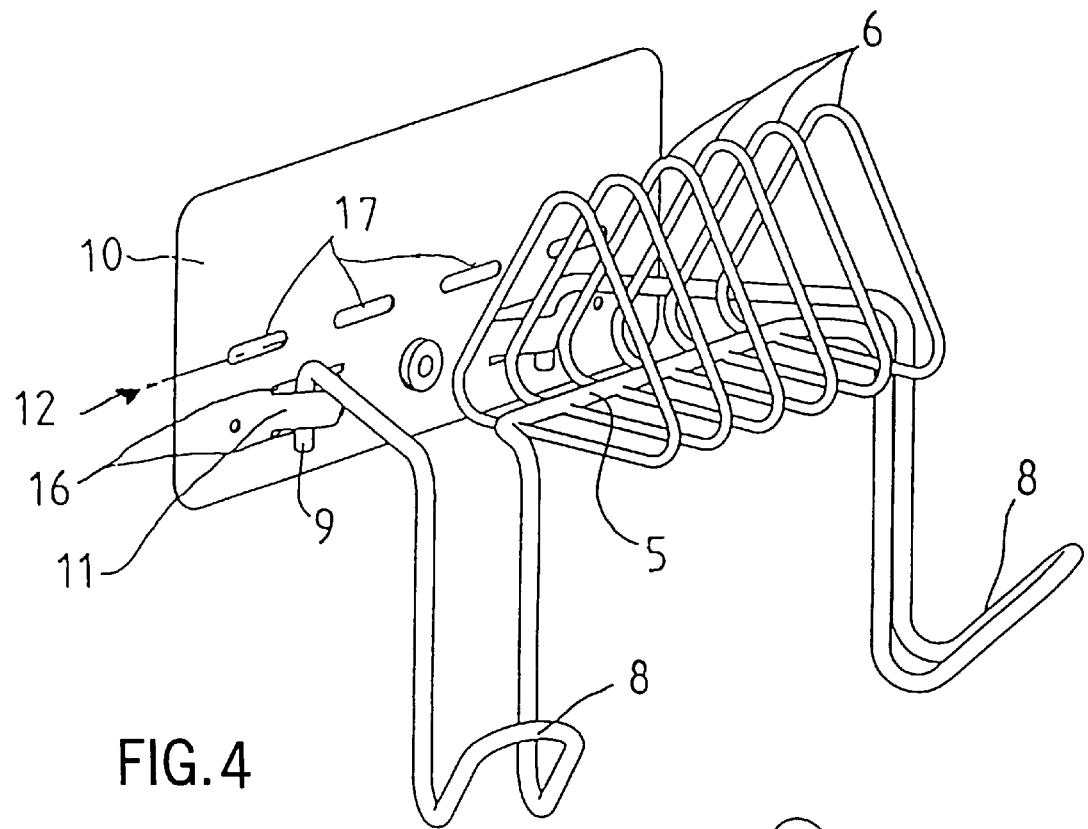
FIGS. 4 and 5 show a rack of the invention in a second embodiment.

FIG. 1 illustrates a suspension rack in medical use, such as for the storage and suspension of cables 1 and/or tubes employed in patient monitoring, anesthesia, etc. The rack includes a frame 2, provided with fastening means 3 for securing the frame 2 to a substantially solid structure 4 and with implements mounted on the frame for the suspension of cables and/or tubes.

The frame 2 includes a bracket element 5, which is adapted to support the cable 1 and/or the tube from below, as shown in FIG. 2. In addition to the bracket element 5, said implements include a cluster or an array of mutually parallel adjacent spacer elements 6 mounted on the bracket element. The spacer elements 6 are spaced from each other by a distance exceeding the thickness of a cable and/or a tube. However, this distance is less than the dimension of a terminal element 7, such as a connector or a sensor unit, transverse to the lengthwise direction of a cable and/or a tube, said terminal element being mounted on the end of a cable and/or a tube. Thus, as shown in FIG. 2, the cable and/or the tube can be placed between two adjacent spacer elements 6 to rest upon the bracket element 5, said terminal element 7 finding its way to said two adjacent spacer elements 6 without being able to slip out through the gap between the spacer elements.

As shown in FIGS. 1–3, the frame two includes two hooks 8, arranged on either side of the cluster of spacer elements 6. The hook 8 can be used for suspending therefrom a cable, a spool of cable, a tube and/or a spool of tube, as shown in FIG. 3.

As shown in FIG. 1, the fastening means 3 for securing the frame 2 to the substantially solid structure 4 include two mutually substantially parallel, spaced-apart fingers 9. Furthermore, the fastening means 3 include a mounting 10, fastenable to the solid structure 4 and provided with fasteners 11 which are adapted to receive therein the fingers 9. In FIGS. 1–3, the mounting 10 comprises an element, wherein the fasteners 11 are in the form of vertical holes having a sufficient depth for receiving the fingers 9.

The spacer elements 6 are loop-shaped, in this case, for the reasons of safety, shaped like a round-cornered triangular loop. The loop need not necessarily be a closed loop, but it can also be open in such a way that there is a gap between the ends of a loop-forming bent wire or rod, with the ends coming very close to each other. The gap may be located at the rear of a loop. The loops can also be given any other shape, e.g. a square, rectangular, elliptical, or circular shape. The spacer element 6 can be fastened to the bracket element 5 of the frame 2 in the front of, in the back of, above, or below the same. The spacer element loop 6 has a vertical height which is at least equal to the diameter of a cable or tube to be suspended therefrom. Likewise, it has a dimension forward which is preferably at least equal to the diameter of a cable or tube to be suspended therefrom.

As depicted in FIG. 3, the suspension rack is also provided with suspenders 14, in this case adhesive tapes. The adhesive tape suspender is removably suspendable upon the loop-shaped spacer element 6. A spool of cable is in turn removably fastenable to this adhesive tape suspender 14. The bottom edge of the spacers 6 is fitted with adhesively gripping tape fasteners, which can be provided side by side with a number of bundles of cable or tube equal to that of the spacers. The adhesive tapes are manufactured in such a manner that one end thereof, constituting a shorter hook portion, can be readily wound around the bottom wire of the spacer 6 and the remaining free, downward hanging adhesive portion can be opened and closed around a spool of cable or tube. If the adhesive tape 14 has a width of about 25–50 mm, the dimensions of the loop 6 will be sized in view of allowing the adhesive tape to extend through the loop.

Figure 5:
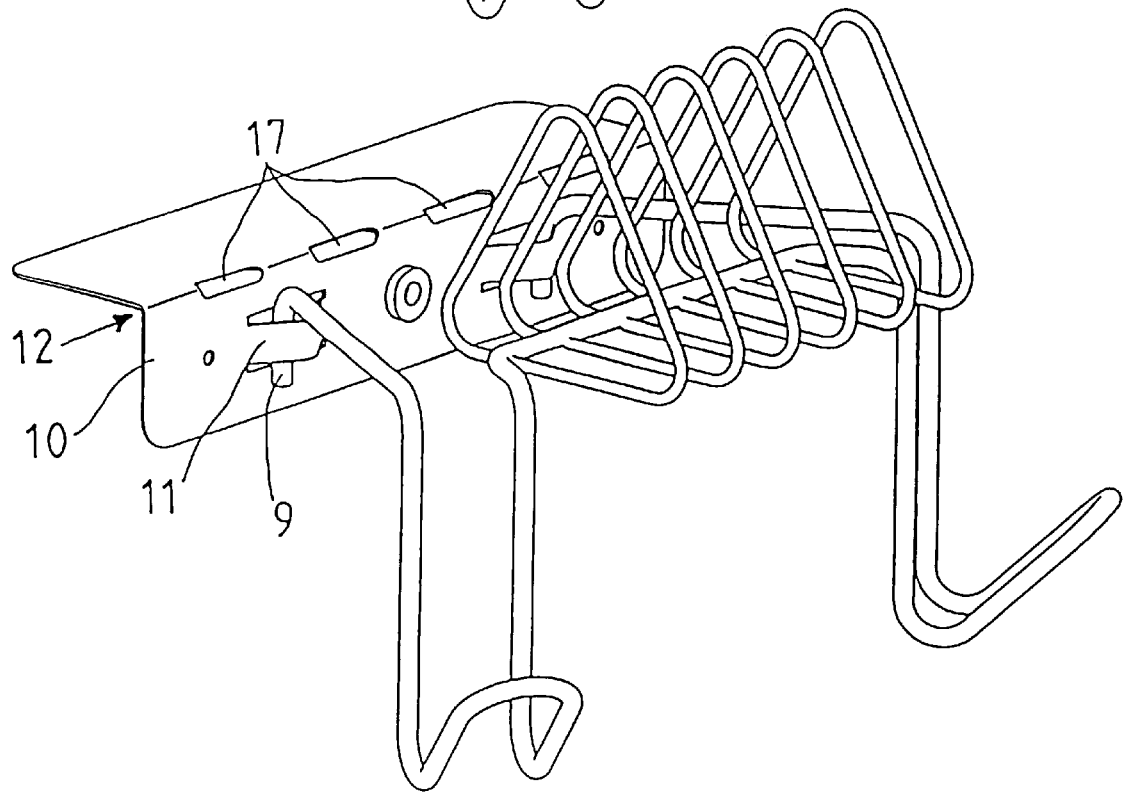

FIGS. 4 and 5 depict a suspension rack embodiment which, in terms of the cluster of spacer elements 6, is structurally essentially similar to the embodiment of FIGS. 1–3. The hooks 8 are positioned somewhat lower than in FIGS. 1–3. What is essential is that the mounting 10 is made of a thin sheet metal. The fastener 11 is provided by punching in the sheet two parallel elongated holes 16 and by stretching the sheet section therebetween outwards for pushing the finger 9 therebehind. The mounting 10 of FIG. 10 can be fastened to a vertical wall. The mounting plate 10 is provided with a bending line 12 weakened by elongated holes 17, along which the mounting plate 10 is foldable to the angular shape of FIG. 5 to be mountable on the edge of a flat surface.

Figure 6:
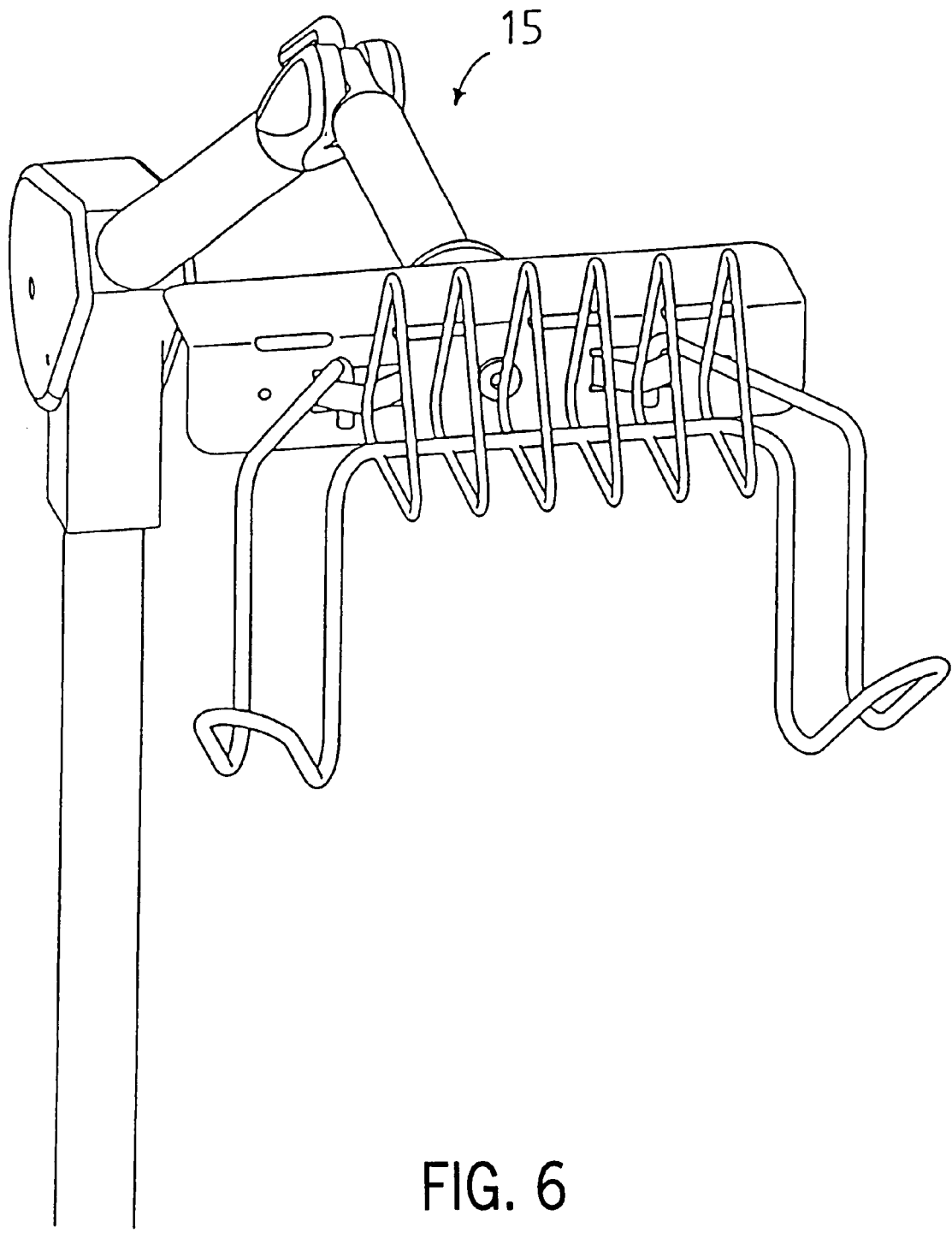
FIG. 6 shows the embodiment of FIG. 5 mounted on the end of an articulated arm.

In FIG. 6, the suspension rack of FIG. 5 is mounted on the free end of an articulated arm 15.

Figure 7:
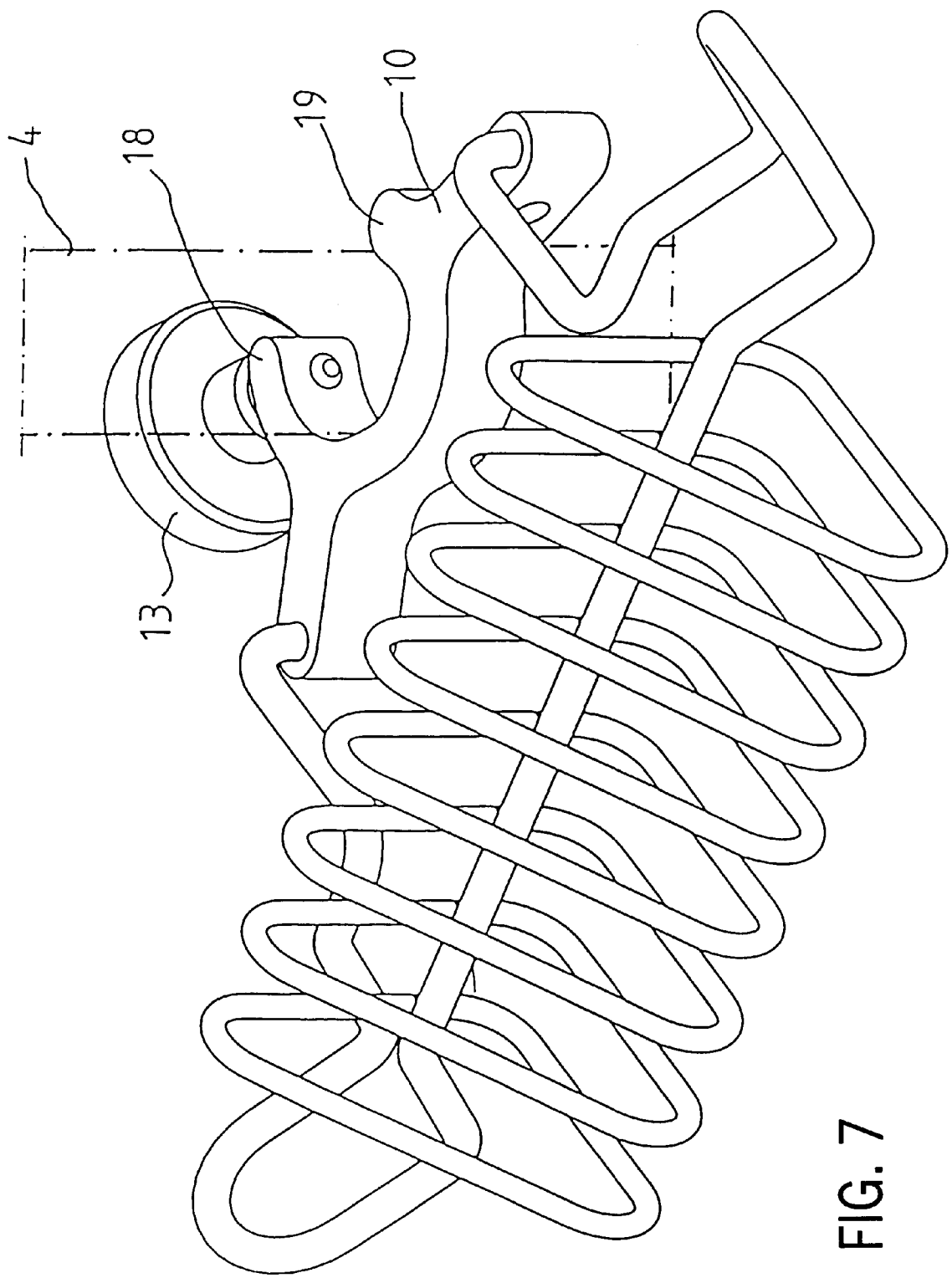
FIG. 7 shows a rack of the invention in a third embodiment.

In FIG. 7, the solid structure 4, to which the mounting 10 is secured, comprises a pipe, a shaft, or the like. In this case, the mounting 9 includes a U-shaped section, which is adapted to receive the pipe, the shaft, or the like between U-legs 18, 19, such that the U-legs extend around the opposite sides of the pipe, the shaft, or the like. In addition, one leg 18 of the mounting 10 is provided with a manual clamping screw 13, which can be turned for pressing the screw point against the outer surface of the pipe, the shaft, or the like.

In the above examples, the frame 2 can be made of a metal rod or wire or a plastic wire. Likewise, the spacer elements 6 can be made of a metal wire or a plastic wire. The frame and spacer elements can be made of a metal wire or rod. Advantageously, the metal wire makes it possible to build a rack by folding it to appropriate configurations. Since the question is about a device intended primarily for hospital use, it is an advantage if such a device can also be easily cleaned and, if necessary, sterilized. Therefore, the rack frame, as well as its spacers, can be entirely coated with a washable and sterilization-resistant material.

The above-described suspension rack with its various fastening elements offers a plurality of advantages. The rack provides flexible attachment possibilities to a variety of vertical or horizontal surfaces and pipes as well as to a cable arm. A variety of possibilities for the suspension and storage of cables: individual, freely hanging cables, spools of cable either for the frame hooks of a bracket element or for loops of adhesive tape, and the accommodation of major spool assemblies of cable behind a row of spacers. When the rack is manufactured from a bent metal wire, the manufacturing costs will be attractive. The rack is easy to clean. The suspension rack is resistant to EtO- and autoclave sterilization.

The bracket element for cables and tubes in a suspension rack can be fastened to a wide variety of sites, partially regardless of the size or shape of the site. This is achieved in such a manner that the system includes separate fastening elements for the bracket element. There is a fastening element for pipe mounting (FIG. 7) as well as for level mounting on vertical surfaces (FIG. 4) or on vertical and horizontal surfaces (FIG. 5). The fastening elements can be secured to their attachment sites by means of a manual screw (a pipe), a two-sided tape or screws (surfaces) or directly by means of a threaded attachment (the end portion of a cable arm, FIG. 6).

The mounting plate shown in FIG. 4 can be fastened to a horizontal flat surface either on top or bottom by means of a separate two-sided tape or by screwing. When the plate is mounted on a horizontal surface, its top portion must be folded by means of bending holes included therein over the edge of the flat surface in such a manner that the holes included in the leading edge of the plate will be in a vertical position. When mounting on a vertical surface, the plate need not be bent.

The invention is not limited to cover just the above exemplary embodiments, but a multitude of modifications are conceivable within the inventive concept defined in the appended claims.

What is claimed is:

1. A rack for receiving a plurality of elongated connecting lines of medical equipment, the connecting lines extending, in use, in proximity to each other and being subject to entanglement with each other, the rack arranging the connecting lines in an orderly fashion to avoid such entanglement, the connecting lines ending in terminal elements having a dimension transverse to the direction of extension of the lines greater than the thickness of the lines, said rack comprising:

a frame (2) having fastening means (3) for securing the frame to a structure (4), said frame including an elongated bracket element (5) lying generally horizontally when the rack is in use, said frame being formed to space said bracket element from the structure; and a plurality of discrete side-by-side spacer elements (6) mounted at spaced intervals along said elongated bracket element (5), said spacer elements and bracket element being formed to allow the connecting lines to be received between said spacer elements for being supported by said bracket element and to extend away from the rack in an orderly fashion in a direction normal to the structure, the spacer elements extending generally vertically from said bracket element and being spaced from each other along the bracket element by a distance which exceeds the thickness of the connecting lines but is less than the transverse dimension of the terminal elements.

2. The rack according to claim 1 wherein said plurality of discrete spacer elements are formed from material strips bent in a closed shape and in a vertical plane, each of said spacer elements being fastened to said bracket element at a point along the length of said material strip, said spacer elements extending vertically and horizontally from said bracket element.

3. The rack according to claim 2 wherein said spacer elements are formed of material strips bent in the shape of triangles and fastened to said bracket element along one of the sides of the triangles.

4. The rack according to claim 1 wherein said spacer elements lie generally parallel to each other.

5. The rack according to claim 2 wherein said spacer elements be generally parallel to each other.

6. The rack according to claim 2 wherein said spacer elements are formed of metal or plastic wire.

7. The rack according to claim 1 wherein said bracket element is formed of metal or plastic wire.

8. The rack according to claim 1 wherein said frame has a hook adjacent to said plurality of spacer elements suitable for receiving a connecting line.

9. The rack according to claim 8 wherein said frame has a pair of hooks, one of which is located adjacent to either side of said spacer elements.

10. The rack according to claim 1 wherein said spaced, discrete spacer elements occupy a portion of the length of said bracket element and wherein said bracket element includes a hook formed in said bracket element outside the occupied portion of said bracket element, said hook being suitable for receiving a coiled connection line.

11. The rack according to claim 2 further including a suspender (14) which is removably suspendable from a spacer element for removably receiving a coil of connecting line.

12. The rack according to claim 1 wherein said fastening means of said frame comprises a pair of mutually parallel, spaced-apart fingers (9) and a mounting means (10) attachable to a solid structure and provided with means (11) adapted to receive the fingers therein.

13. The rack according to claim 12 wherein said mounting means is made of a thin sheet material provided with a bending line (12) for bending said mounting means therealong.

14. The rack according to claim 12 wherein said mounting means (10) comprises a U-shaped element adapted to receive a tubular element and provided with clamping means for fastening the mounting means to the tubular element.

* * * * *